(12) United States Patent
Jung et al.

(10) Patent No.: US 9,399,007 B2
(45) Date of Patent: Jul. 26, 2016

(54) HIGH MOISTURIZING CLEANSING COMPOSITION CONTAINING A LAMELLAR PHASE

(71) Applicant: AMOREPACIFIC CORPORATION, Seoul (KR)

(72) Inventors: Chang Jo Jung, Yongin-si (KR); Dae Kyeong Kim, Yongin-si (KR); John Hwan Lee, Yongin-si (KR); Wang Gi Kim, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 11 days.

(21) Appl. No.: 14/349,775

(22) PCT Filed: Oct. 8, 2012

(86) PCT No.: PCT/KR2012/008131
§ 371 (c)(1),
(2) Date: Apr. 4, 2014

(87) PCT Pub. No.: WO2013/051914
PCT Pub. Date: Apr. 11, 2013

(65) Prior Publication Data
US 2014/0271956 A1    Sep. 18, 2014

(30) Foreign Application Priority Data

Oct. 7, 2011 (KR) .................. 10-2011-0102416

(51) Int. Cl.
| | | |
|---|---|---|
| C11D 3/43 | (2006.01) |
| C11D 7/22 | (2006.01) |
| A61K 8/34 | (2006.01) |
| C11D 1/12 | (2006.01) |
| C11D 1/75 | (2006.01) |
| C11D 1/83 | (2006.01) |
| C11D 17/00 | (2006.01) |
| A61K 8/92 | (2006.01) |
| A61Q 19/00 | (2006.01) |

(52) U.S. Cl.
CPC .............. *A61K 8/342* (2013.01); *A61K 8/922* (2013.01); *A61Q 19/007* (2013.01); *C11D 1/12* (2013.01); *C11D 1/75* (2013.01); *C11D 1/83* (2013.01); *C11D 17/0017* (2013.01); *C11D 17/0026* (2013.01)

(58) Field of Classification Search
CPC ...... C11D 3/0094; C11D 3/2013; C11D 3/43; C11D 7/22; C11D 7/261; C11D 7/262; C11D 17/0017; C11D 1/667
See application file for complete search history.

(56) References Cited

U.S. PATENT DOCUMENTS

| | | | |
|---|---|---|---|
| 5,952,286 A | 9/1999 | Puvvada et al. | |
| 7,081,254 B1* | 7/2006 | Hiraki et al. ................ | 424/450 |
| 2004/0091446 A1 | 5/2004 | Massaro et al. | |
| 2005/0037036 A1* | 2/2005 | Nielsen et al. ............... | 424/401 |
| 2005/0129639 A1* | 6/2005 | Quemin ........................ | 424/63 |
| 2006/0140888 A1* | 6/2006 | Ohashi et al. ................ | 424/62 |
| 2007/0286835 A1* | 12/2007 | Park et al. ................... | 424/70.22 |
| 2008/0107679 A1* | 5/2008 | Dilallo et al. ............ | 424/195.17 |
| 2008/0139434 A1 | 6/2008 | Basappa et al. | |
| 2011/0212041 A1* | 9/2011 | Tohi et al. ..................... | 424/62 |
| 2012/0201902 A1* | 8/2012 | Modak et al. ................ | 424/618 |
| 2014/0100276 A1* | 4/2014 | Orita et al. ................... | 514/552 |

FOREIGN PATENT DOCUMENTS

| | | |
|---|---|---|
| KR | 10-2001-0039678 A | 5/2001 |
| KR | 10-0439932 B1 | 9/2004 |
| KR | 10-2005-0074548 A1 | 7/2005 |
| KR | 10-2009-0087470 A | 8/2009 |

OTHER PUBLICATIONS

International Searching Authority International Search Report for PCT/KR2012/008131 dated Mar. 29, 2013.

* cited by examiner

*Primary Examiner* — Charles Boyer
(74) *Attorney, Agent, or Firm* — Sughrue Mion, PLLC

(57) ABSTRACT

The present invention relates to a lamellar structure which stabilizes oil and to a cleansing composition comprising the lamellar structure. More particularly, the present invention relates to a lamellar structure, which stabilizes oil to be used in a cleansing composition so that high-content oil is converted to a lamellar phase and contained in a composition. The present invention also relates to a cleansing composition which comprises the lamellar structure which enables the composition to contain high-content oil in a stable manner and to thus provide superior moisturizing ability.

12 Claims, 1 Drawing Sheet

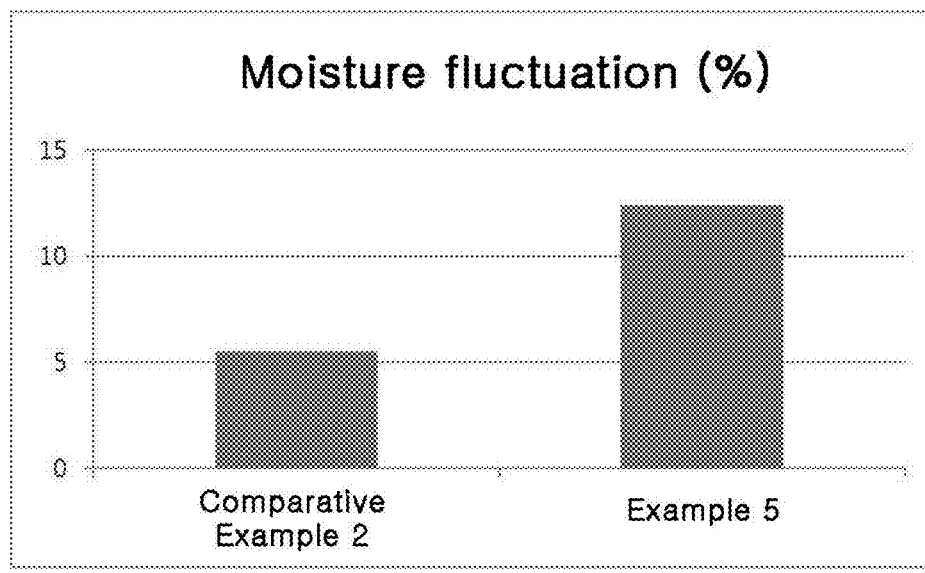

HIGH MOISTURIZING CLEANSING COMPOSITION CONTAINING A LAMELLAR PHASE

CROSS REFERENCE TO RELATED APPLICATIONS

This application is a National Stage of International Application No. PCT/KR2012/008131 filed Oct. 8, 2012, claiming priority based on Korean Patent Application No. 10-2011-0102416 filed Oct. 7, 2011, the contents of all of which are incorporated herein by reference in their entirety.

TECHNICAL FIELD

The present invention relates to a lamellar structure that stabilizes oil and to a cleansing composition comprising the lamellar structure, and more particularly to a lamellar structure that stabilizes oil in a cleansing composition to form a lamellar phase so as to enable a large amount of oil to be contained in the composition and to a cleansing composition containing the lamellar structure that enables a large amount of oil contained therein to be maintained in a stable state so as to provide excellent moisturizing ability.

BACKGROUND ART

Generally, the use of cleansers in shower causes skin's tightening, itching and troubles due to their excessive cleansing effects, and to solve such phenomena, moisturizers or the like are applied to the skin after cleansing. However, this application of moisturizers is troublesome and causes sticky feeling. To solve such problems, in prior art, a large amount of oil was added to cleansers to provide cleansers having increased moisturizing ability.

However, in order for cleansers to have a high oil content, a highly viscous lamellar phase is required. To make this lamellar phase, the use of structuring agents such as lauric acid or trihydroxy stearate is required. However, such structuring agents have a problem in that they cause stability-related problems in some environments.

DISCLOSURE OF INVENTION

Technical Problem

Accordingly, the present inventors have found that, when a high content of oil is used together with a lamellar structure, it is stable even in a cycling test at a temperature raging from −10° C. to 45° C., which is a severe condition, thereby completing the present invention.

Therefore, it is an object of the present invention to provide a lamellar structure capable of stabilizing oil.

Another object of the present invention is to provide a cleansing composition containing the lamellar structure that enables a large amount of oil contained therein to be maintained in a stable state so as to have high moisturizing ability.

Solution to Problem

In order to achieve the above objects, the present invention provides a lamellar structure comprising a fatty alcohol having 14 to 18 carbon atoms.

The present invention also provides a cleansing composition containing the lamellar structure and oil.

Advantageous Effects of Invention

The lamellar structure of the present invention can stabilize a high content of oil, and the use thereof in a cleansing composition can provide a stable cleansing composition having increased skin-moisturizing ability, which does not cause skin drying or tightening after its use in shower.

BRIEF DESCRIPTION OF DRAWINGS

FIG. 1 is a graphic diagram showing the percent increase in moisture content after the application of compositions of Comparative Example 2 and Example 5 to the skin.

MODE FOR THE INVENTION

The present invention provides a lamellar structure that stabilizes oil that is used in a composition. The lamellar structure of the present invention may comprise a fatty alcohol having 14 to 18 carbon atoms. The fatty alcohol that is used in the present invention may be a fatty alcohol from palm oil or coconut oil. Specifically, the fatty alcohol may be myristyl alcohol, cetyl alcohol, or stearyl alcohol. If the fatty alcohol has less than 14 carbon atoms, it will not easy to form a liquid phase, and if the fatty alcohol has more than 18 carbon atoms, it will reduce the foaming ability of the composition due to the long carbon chain length, resulting in a decrease in the cleansing ability of the composition.

The present invention provides a cleansing composition having a high oil content that provides excellent moisturizing ability. To stabilize the high content of oil in the composition, the composition contains a lamellar structure as described above. Preferably, the composition of the present invention is in a creamy state and may be used to cleanse the human body.

The content of the lamellar structure in the cleansing composition of the present invention is 0.1-10 wt %, and preferably 1-5 wt %, based on the total weight of the composition. In this content range, the stability and sensory feel of the formulation can be maximized.

In addition, the cleansing composition of the present invention may further comprise an oil structure stabilizer. The oil structure stabilizer that is used in the present invention may be a sorbitan derivative comprising a fatty acid or oil bounded to sorbitol, for example, sorbitan stearate. Specific examples of the oil structure stabilizer include sorbitan laurate, sorbitan palmitate, sorbitan stearate, sorbitan tristearate, sorbitan isostearate, sorbitan cocoate, sorbitan oleate, and sorbitan olivate. The oil structure stabilizer has a structure represented by the following formula 1:

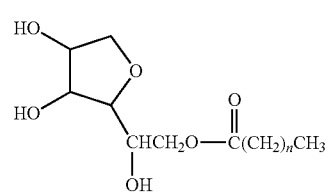

Formula 1

The content of the oil structure stabilizer in the cleansing composition of the present invention is 0.1-10 wt %, and preferably 1-5 wt %, based on the total weight of the oil contained in the composition. In this content range, the stability and sensory feel of the formulation can be maximized.

The oil that is used in the cleansing composition of the present invention serves to increase the moisturizing ability of the cleansing composition. Specifically, the oil may comprise one or a mixture of two or more selected from among vegetable oils such as sunflower seed oil, grape seed oil, bean oil, palm oil, coconut oil or canola oil; mineral oils such as petrolatum; and silicone oil.

The content of the oil in the composition is 1-50 wt %, and preferably 5-30 wt %, based on the total weight of the composition. In this content range, the stability and sensory feel of the formulation can be maximized.

The cleansing composition of the present invention comprises a surfactant. The surfactant that is used in the present invention is an anionic surfactant. Particularly, an anionic surfactant having good foaming ability and excellent cleansing ability may be used, such as an alkyl sulfate having 12 carbon atoms (lauryl) to 18 carbon atoms (stearyl), or a sulfate having 2 to 5 polyoxyether groups added thereto. In addition, anionic surfactants having excellent foaming ability and cleansing ability may be used in the present invention. Specific examples of anionic surfactants having excellent foaming ability and cleansing ability include aliphatic sulfonates, aromatic sulfonates, alkyl sulfates, alkyl ether sulfates, alkyl sulfosuccinates, alkyl and acyl taurates, alkyl and acyl sarcosinates, sulfoacetates, $C_8$-$C_{22}$ alkyl phosphates, alkyl phosphate esters, alkoxy alkyl phosphate esters, acyl lactates, $C_8$-$C_{22}$ monoalkyl succinates and malates, sulfoacetates, acyl isethionates, carboxylates, etc.

Further, in the present invention, the above-described anionic surfactant may be used in a mixture with an amphoteric surfactant, a non-ionic surfactant or the like. An amphoteric surfactant that may be used in the present invention is not specifically limited, as long as it has the effect of increasing the foaming ability of the composition. Examples of amphoteric surfactants that may be used in the present invention include alkyl betaine, alkyl sultaine, alkyl amidopropyl betaine, alkyl amidopropyl hydroxy sultaine, alkyl amphoacetate, alkyl diamphoacetate, etc. In addition, a non-ionic surfactant that may be used in the present, invention is specifically not limited, as long as it has the effect of increasing the foaming ability of the composition. Examples of non-ionic surfactants that may be used in the present invention include alkyl glucose amide, alkyl glucose ester, polyoxyethylene ester, fatty alkane amide, alkyl amine oxide, alkyl polyglucoside, polyoxyethylene ester of fatty acid, etc.

The content of the surfactant in the cleansing composition is 5-30 wt %, and preferably 9-15 wt %, based on the total weight of the composition. This is because a surfactant content of less than 5 wt % is undesirable in terms of the foaming ability and sensory feel of the composition, and a surfactant content of more than 30 wt % is undesirable in terms of the sensory feel and price of the composition.

In addition, the composition of the present invention may, if necessary, further comprise a thickener, a foam stabilizer, a chelating agent, a conditioning agent, etc. For example, the thickener may be a salt, and the foam stabilizer may be lauric acid. Further, the chelating agent may be EDTA-2Na, and the conditioning agent may be glycerin, a cationic guar polymer or the like.

The composition of the present invention may be formulated as a creamy cleansing composition, for example, but is not specifically limited thereto.

Mode for Invention

Hereinafter, the present invention will be described in further detail with reference to examples and test examples, but the scope of the present invention is not limited only to these examples.

Reference Example 1

Preparation of Compositions of Comparative Examples 1 to 4 and Examples 1 to 5

The components shown in Tables 1 and 2 below were mixed with each other according to a conventional method known in the art to prepare cleansing compositions. Specifically, compositions of Comparative Examples 1 to 4 and Examples 1 to 3 were emulsified using a paddle mixer, and compositions of Examples 4 and 5 were emulsified using a homomixer. The compositions of Examples 1 to 5 were prepared using fatty alcohols having different carbon chain lengths. In addition, the compositions of Examples 3 and 4 were prepared by performing an emulsifying process using a paddle mixer and a homomixer, respectively, and the composition of Example 5 was prepared by additionally using sorbitan stearate.

TABLE 1

| Functions | Components (wt %) | Comp. Example 1 | Comp. Example 2 | Comp. Example 3 | Example 1 | Example 2 |
|---|---|---|---|---|---|---|
| Solvent | Purified water | To 100 | To 100 | To 100 | To 100 | To 100 |
| Surfactant | Ammonium laureth sulfate | 10.75 | 10.75 | 10.75 | 10.75 | 10.75 |
| | Cocamidopropyl betaine | 5.1 | 5.1 | 5.1 | 5.1 | 5.1 |
| | Cocamide MEA | 5 | 5 | 5 | 5 | 5 |
| Lamellar structure | Laurie acid | 3.5 | — | — | — | — |
| | Lauryl alcohol | — | — | 3.5 | — | — |
| | Myristyl alcohol | — | — | — | 3.5 | — |
| | Cetyl alcohol | — | — | — | — | 3.5 |
| Foaming enhancer | Laurie acid | 1.5 | — | 1.5 | 1.5 | 1.5 |
| Oil | Sunflower seed oil | 20 | — | 20 | 20 | 20 |
| Conditioning agent | Glycerin | 5 | 5 | 5 | 5 | 5 |
| | Guar hydroxypropyltrimonium chloride | 0.5 | 0.5 | 0.5 | 0.5 | 0.5 |
| Thickener | NaCl | 2 | 2 | 2 | 2 | 2 |
| Chelating agent | EDTA-2Na | 0.05 | 0.05 | 0.05 | 0.05 | 0.05 |
| Other materials | Fragrance | 1 | 1 | 1 | 1 | 1 |
| | Preservative | q.s. | q.s. | q.s. | q.s. | q.s. |
| Emulsification process condition. | Mixer | Paddle | Paddle | Paddle | Paddle | Paddle |

TABLE 2

| Functions | Components (wt %) | Example 3 | Example 4 | Example 5 | Comp. Example 4 |
|---|---|---|---|---|---|
| Solvent | Purified water | To 100 | To 100 | To 100 | To 100 |
| Surfactant | Ammonium laureth sulfate | 10.75 | 10.75 | 10.75 | 10.75 |
| | Cocamidopropyl betaine | 5.1 | 5.1 | 5.1 | 5.1 |
| | Cocamide MEA | 5 | 5 | 5 | 5 |
| Lamella structure | Stearyl alcohol | 3.5 | 3.5 | 3.5 | — |
| | Behenyl alcohol | — | — | — | 3.5 |
| Oil structure stabilizer | Sorbitane stearate | — | — | 1 | — |
| Foaming enhancer | Lauric acid | 1.5 | 1.5 | 1.5 | 1.5 |
| Oil | Sunflower seed oil | 20 | 20 | 20 | 20 |
| Conditioning agent | Glycerin | 5 | 5 | 5 | 5 |
| | Guar hydroxypropyltrimonium chloride | 0.5 | 0.5 | 0.5 | 0.5 |
| Thickener | NaCl | 2 | 2 | 2 | 2 |
| Chelating agent | EDTA-2Na | 0.05 | 0.05 | 0.05 | 0.05 |
| Other materials | Fragrance | 1 | 1 | 1 | 1 |
| | Preservative | q.s. | q.s. | q.s. | q.s. |
| Emulsification process condition | Mixer | Paddle | Homomixer | Homomixer | Paddle |

Test Example 1

Measurement of Viscosity

1) Measurement of Viscosity

Brookfield viscometer LV DVI+ and RVT models were used. At a viscosity of 40000 cps or lower, the LV DVI+ model was used, and at a viscosity of 40000 cps or higher, the RVT model was used. The measurement of viscosity was performed at 30° C.

2) Cycling Test

A cycling test consisted of maintenance at −10° C. for 11 hours, then heating to 45° C. for 1 hour, then maintenance at 45° C. for 11 hours, and then cooling −10° C. for 1 hour. After the cycling test was performed at 1 cycle/day for 10 days, each composition was allowed to stand at 30° C. for 24 hours, followed by measurement of the viscosity. In addition, in order to measure the stability of each composition, whether phase separation occurred was observed after performing the above-described cycling test at 1 cycle/day for 1 month.

The results are shown in Table 3 below.

TABLE 3

Viscosity and stability

| | Comp. Example 1 | Comp. Example 3 | Comp. Example 4 | Example 1 |
|---|---|---|---|---|
| Viscosity after 1 day | 37000 | 32000 | 42000 | 34900 |
| Viscosity after 10 days | 44000 | 11000 | 40000 | 15000 |
| Cycling viscosity −10/+45° C. (10 cycles/10 days) | 18700 | 9000 | 25000 | 13200 |
| Stability (cycling test performed for 1 month) | Separated | Separated | Stable | Stable |

| | Example 2 | Example 3 | Example 4 | Example 5 |
|---|---|---|---|---|
| Viscosity after 1 day | 29500 | 37000 | 280000 | 380000 |
| Viscosity after 10 days | 42000 | 35000 | 280000 | 400000 |
| Cycling viscosity −10/+45° C. (10 cycles/10 days) | 170000 | 22000 | 23000 | 400000 |
| Stability (cycling test performed for 1 month) | Stable | Stable | Stable | Stable |

As can be seen in Table 3 above, the compositions of Examples 1 to 5 that comprise fatty alcohol as the lamellar structure were stable even after 10 days of the cycling tests, unlike the composition of Comparative Example 1 that comprises fatty acid as the lamellar structure. In addition, the composition of Comparative Example 3 that comprises lauryl alcohol having 12 carbon atoms had inferior stability.

Further, it can be seen that, in the case of Examples 4 and 5 in which the homomixer was used in the emulsification process, the initial viscosity was high compared to the case in which the paddle mixer was used. In addition, it can be seen that the composition of Example 5 that further contains sorbitan stearate showed oil stability and did not show a decrease in viscosity in the cycling test.

Test Example 2

Comparison of Moisturizing Ability

In order to measure the moisturizing ability of the oil-containing composition of the present invention, moisturizing ability was compared between the composition of Comparative Example 2 that contains no oil and the composition of Example 5 that contains oil. The evaluation of moisturizing ability was performed using a corneometer capable of measuring moisture content. Specifically, a selected portion of the forearm was measured three times before application of each sample, and 1 g of each sample was applied thereto. Then, 1 g of tap water was added to the selected portion, which was then rubbed 30 times, after which the sample was rinsed out. After 30 minutes, the selected portion was measured three times with corneometer.

Measurement Method Using Corneometer

Moisturizing ability was measured by measuring the ionic strength of water present in the epidermis of the skin by a sensor and expressing the measured value as a numerical value.

1. The probe of a corneometer was placed on the skin portion to be measured.
2. When the probe was pressed against the skin, the capacitance of the skin was displayed as a numerical value on the monitor through the sensor.
3. Measurement was repeated on different skin portion.
4. After each measurement, the sensor was wiped with tissue paper such as Kimwipes.

The results of the measurement are shown in Table 4 below, and the results of measurement of the percent change in moisture content are shown in FIG. 1.

TABLE 4

|  | Comparative Example 2 | Example 5 |
|---|---|---|
| Before treatment | 23.4 | 23.5 |
| After treatment | 24.7 | 26.4 |
| Percent increase | 5.5 | 12.4 |

As can be seen in Table 4 above, the composition of Example 5 showed a greater increase in moisture content after treatment compared to the composition of Comparative Example 2, suggesting that the composition of the present invention is more effective in moisturizing the skin.

Test Example 3

Comparison of Foaming Ability

The foaming ability of each composition was evaluated on a five-point scale by examining the texture and amount of foams upon use and the overall satisfaction of foams. The results of the evaluation are shown in Table 5 below.

TABLE 5

| Evaluation of foaming ability | Example 1 | Example 2 | Example 3 | Example 4 | Example 5 | Comp. Example 4 |
|---|---|---|---|---|---|---|
| Amount of foams | 4.5 | 4.3 | 4.3 | 4.6 | 4.5 | 3.2 |
| Texture of foams | 4 | 4.2 | 4.2 | 4.3 | 4.3 | 2.5 |
| Satisfaction | 4.3 | 4.3 | 4.3 | 4.5 | 4.4 | 2.9 |

As can be seen in Table 5 above, the compositions of Examples 1 to 5 of the present invention obtained very high scores in relation to the amount and texture of foams and the overall satisfaction of foams. However, the composition of Comparative Example 4 that comprises a $C_{22}$ behenyl alcohol as the lamellar structure showed a significantly low foaming ability, suggesting that it has poor cleansing ability, even though oil in the composition was stable.

The invention claimed is:

1. A skin cleansing composition containing
    a lamellar-forming component,
    an oil, and
    an oil structure stabilizer selected from the group consisting of sorbitan laurate, sorbitan palmitate, sorbitan stearate, sorbitan tristearate, sorbitan isostearate, sorbitan cocoate, sorbitan oleate, and sorbitan olivate,
    wherein the lamellar-forming component consists of a fatty alcohol having 14 to 18 carbon atoms and is contained in an amount of 0.1-10 wt % based on the total weight of the composition;
    wherein the oil is contained in an amount of 20-50 wt % based on the total weight of the composition; and
    wherein the oil structure stabilizer is contained in an amount of 0.1-10 wt % based on the weight of the oil.

2. The cleansing composition of claim 1, wherein the oil is one or more selected from the group consisting of sunflower seed oil, grape seed oil, bean oil, palm oil, coconut oil, canola oil, petrolatum, and silicone oil.

3. The cleansing composition of claim 1, wherein the composition further contains a surfactant.

4. The cleansing composition of claim 3, wherein the surfactant is one or more selected from the group consisting of an anionic surfactant, an amphoteric surfactant and a non-ionic surfactant.

5. The cleansing composition of claim 4, wherein the anionic surfactant is an alkyl sulfate having 12 to 18 carbon atoms or a sulfate having 2 to 5 polyoxyether groups attached thereto.

6. The cleansing composition of claim 4, wherein the amphoteric surfactant is one or more selected from the group consisting of alkyl betaine, alkyl sultaine, alkyl amidopropyl betaine, alkyl amidopropyl hydroxy sultaine, alkyl amphoacetate, and alkyl diamphoacetate.

7. The cleansing composition of claim 4, wherein the non-ionic surfactant is one or more selected from the group consisting of alkyl glucose amides, alkyl glucose polyoxyethylene esters, fatty alkane amides, alkyl amine oxides, alkyl polyglucosides, and polyoxyethylene esters of fatty acids.

8. The cleansing composition of claim 3, wherein the surfactant is contained in an amount of 5-30 wt % based on the total weight of the composition.

9. The cleansing composition of claim 1, wherein the lamellar-forming component is contained in an amount of 1-5 wt % based on the total weight of the composition.

10. The cleansing composition of claim 1, wherein the oil is contained in an amount of from 20-30 wt % based on the total weight of the composition.

11. The cleansing composition of claim 1, wherein the oil structure stabilizer is contained in an amount of 1-5 wt % based on the weight of the oil.

12. A skin cleansing composition consisting of:
    a lamellar-forming component,
    an oil structure,
    an oil stabilizer selected from the group consisting of sorbitan laurate, sorbitan palmitate, sorbitan stearate, sorbitan tristearate, sorbitan isostearate, sorbitan cocoate, sorbitan oleate, and sorbitan olivate,
    a surfactant,
    water, and
    at least one additive selected from the group consisting of a thickener, a foam stabilizer, a chelating agent, a conditioning agent, a fragrance, and a preservative,
    wherein the lamellar-forming component consists of a fatty alcohol having 14 to 18 carbon atoms and is contained in an amount of 0.1-10 wt % based on the total weight of the composition;
    wherein the oil is contained in an amount of 1-50 wt % based on the total weight of the composition; and
    wherein the oil structure stabilizer is contained in an amount of 0.1-10 wt % based on the weight of the oil.

* * * * *